United States Patent
Dzau et al.

(10) Patent No.: US 6,352,555 B1
(45) Date of Patent: Mar. 5, 2002

(54) METHODS FOR IMPLANTING CELLS

(75) Inventors: Victor J. Dzau; Richard E. Pratt; Michael J. Mann, all of Newton; Afshin Ehsan; Daniel P. Griese, both of Boston, all of MA (US)

(73) Assignee: The Brigham and Womens Hospital, Inc., Boston, MA (US)

( * ) Notice: Subject to any disclaimer, the term of this patent is extended or adjusted under 35 U.S.C. 154(b) by 0 days.

(21) Appl. No.: 09/349,344

(22) Filed: Jul. 8, 1999

Related U.S. Application Data

(60) Provisional application No. 60/092,358, filed on Jul. 10, 1998.

(51) Int. Cl.[7] ................................................. A61F 2/06

(52) U.S. Cl. ....................... 623/1.39; 623/1.4; 623/1.41; 600/36; 424/422

(58) Field of Search ................................. 623/1.39, 1.4, 623/1.41, 901, 921; 600/36; 264/209.1; 424/422, 93.21, 127, 288.8, 289.3; 435/240.2, 371; 935/70, 71

(56) References Cited

U.S. PATENT DOCUMENTS

| | | | |
|---|---|---|---|
| 4,505,266 A | * | 3/1985 | Yannas et al. ............... 128/898 |
| 5,171,261 A | | 12/1992 | Noishiki et al. |
| 5,387,236 A | | 2/1995 | Noishiki et al. |
| 5,433,909 A | | 7/1995 | Martakos et al. |
| 5,512,474 A | | 4/1996 | Clapper et al. |
| 5,628,781 A | | 5/1997 | Williams et al. |
| 5,652,225 A | | 7/1997 | Isner |
| 5,665,114 A | | 9/1997 | Weadock et al. |
| 5,674,722 A | | 10/1997 | Mulligan et al. |
| 5,691,203 A | | 11/1997 | Katsuen et al. |
| 5,716,660 A | | 2/1998 | Weadock et al. |
| 5,726,152 A | | 3/1998 | Bayne et al. |
| 5,744,515 A | | 4/1998 | Clapper |
| 5,770,193 A | | 6/1998 | Vacanti et al. |
| 5,830,879 A | | 11/1998 | Isner |
| 5,980,887 A | | 11/1999 | Isner et al. |

FOREIGN PATENT DOCUMENTS

| | | |
|---|---|---|
| WO | WO 98/19712 | 5/1998 |

OTHER PUBLICATIONS

Asahara et al., "Synergistic Effect of Vascular Endothelial Growth Factor and Basic Fibroblast Growth Factor on Angiogenesis In Vivo," Supplement II, Circulation 92:365–371, 1995.

Bull et al., "Cellular Origin and Rate of Endothelial Cell Coverage of PTFE Grafts," J. Surgical Res. 58:58–68, 1995.

Cameron et al., "High Porosity PTFE Improves Endothelialization of Arterial Grafts Without Increasing Early Thrombogenicity," J. Cardiovasc. Surg. 34:281–285, 1993.

Jarrell and Williams, "Microvessel Derived Endothelial Cell Isolation, Adherence, and Monolayer Formation for Vascular Grafts," J. Vasc. Surg. 13:733–734, 1991.

(List continued on next page.)

Primary Examiner—Corrine McDermott
Assistant Examiner—Choon P. Koh
(74) Attorney, Agent, or Firm—Clark & Elbing LLP

(57) ABSTRACT

Disclosed herein is a method for implanting cells onto a prosthesis, including the steps of: (a) providing a prosthesis including a porous tube, where at least 25% of the pores on the inner surface of the tube have diameters of more than about 40 $\mu$m, at least 25% of the pores on the outer surface of the tube have diameters of less than about 30 $\mu$m, and the tube includes a substantially continuous layer of a biocompatible material; (b) contacting the prosthesis with a suspension of cells; and (c) providing a pressure differential between the inner surface and the outer surface, whereby the cells are retained in the pores of the inner surface. Also disclosed herein are methods for culturing cells for implantation.

12 Claims, 2 Drawing Sheets

OTHER PUBLICATIONS

Jarrell et al., "Optimization of Human Endothelial Cell Attachment to Vascular Graft Polymers," J. Biomech. Eng. 113:120–122, 1991.

Jarrell et al., "Use of Freshly Isolated Capillary Endothelial Cells for the Immediate Establishment of a Monolayer on a Vascular Graft at Surgery," Surgery 100:392–399, 1986.

Noishiki et al., "Autocrine Angiogenic Vascular Prosthesis with Bone Marrow Transplantation," Nature Medicine 2:90–93, 1996.

Park et al., "Thrombus–Free, Human Endothelial Surface in the Midregion of a Dacron Vascular Graft in the Splanchnic Venous Circuit—Observations after Nine Months of Implantation," J. Vasc. Surg. 11:468–475, 1990.

Radomski et al., "Effects of In Vitro Aging on Human Endothelial Cell Adherence to Dacron Vascular Graft Material," J. Surg. Res. 47–173–177, 1989.

Radomski et al., "Initial Adherence of Human Capillary Endothelial Cells to Dacron," J. Surg. Res. 42:133–140, 1987.

Schweitzer et al., "Isolation and Culture of Human Bone Marrow Endothelial Cells," Exp. Hematology 23:41–48, 1995.

Stopeck et al., "Transfer and Expression of the Interferon Gamma Gene in Human Endothelial Cells Inhibits Vascular Smooth Muscle Cell Growth In Vitro," Cell Transplantation 6:1–8, 1997.

Takahashi et al., "Ischemia– and Cytokine–Induced Mobilization of Bone Marrow–Derived Endothelial Progenitor Cells for Neovascularization," Nature Medicine 5:434–438, 1999.

Tischer et al., "The Human Gene for Vascular Endothelial Growth Factor," J. Biological Chemistry 266:11947–11954, 1991.

Tischer et al., "Vascular Endothelial Growth Factor: A New Member of the Platelet–Derived Growth Factor Gene Family," Biochem. Biophys. Res. Comm. 165:1198–1206, 1989.

Tsuchida et al., "Healing Mechanisms of High–Porosity PTFE Grafts: Significance of Transmural Structure," J. Surg. Res. 71:187–195, 1997.

Tsuchida et al., "In Vivo Study of a High–Porosity Polytetrafluoroethylene Graft: Endothelialization, Fluid Leakage, and the Effect of Fibrin Glue Sealing," J. Invest. Surgery 6:509–518, 1993.

Westerband et al., "Immunocytochemical Determination of Cell Type and Proliferation Rate in Human Vein Graft Stenoses," J. Vasc. Surg. 25:64–73, 1997.

Williams, "Endothelial Cell Transplantation," Cell Transplantation 4:401–410, 1995.

Williams et al., "Formation of a Multilayer Cellular Lining on a Polyurethane Vascular Graft Following Endothelial Cell Sodding," J. Biomed. Materials Res. 26:103–117, 1992.

Williams et al., "Adult Human Endothelial Cell Compatibility with Prosthetic Graft Material," J. Surg. Res. 38:618–629, 1985.

Williams et al., "Endothelial Cell Transplantion onto Polymeric Arteriovenous Grafts Evaluated Using a Canine Model," J. Invest. Surg. 7:503–517, 1994.

Williams et al., "Human Microvessel Endothelial Cell Isolation and Vascular Graft Sodding in the Operating Room," Annals Vasc. Surg. 3:146–152, 1989.

Williams et al., "Origin of Endothelial Cells That Line Expanded Polytetrafluoroethylene Vascular Grafts Sodded with Cells from Microvascularized Fat," J. Vasc. Surg. 19:594–604, 1994.

Williams et al., "Microvascular Endothelial Cell Sodding of ePTFE Vascular Grafts: Improved Patency and Stability of the Cellular Lining," J. Biomed. Materials Res. 28:203–212, 1994.

Williams et al., "Formation of a Functional Endothelium on Vascular Grafts," J. Electron Microscopy 19:439–451, 1991.

Williams et al., "Liposuction–Derived Human Fat Used for Vascular Graft Sodding Contains Endothelial Cells and Not Mesothelial Cells as the Major Cell Type," J. Vasc. Surg. 19:916–923, 1994.

Wilson et al., "Implantation of Vascular Grafts Lined with Genetically Modified Endothelial Cells," Science 244:344–346, 1989.

Yamamoto et al., "Human VEGF Gene Transfer into Vascular Prosthesis," Abstract from the $69^{th}$ Scientific Sessions, #3721.

* cited by examiner

METHODS FOR IMPLANTING CELLS

CROSS REFERENCE TO RELATED APPLICATIONS

This application claims benefit of U.S. provisional patent application, 60/092,358, filed Jul. 10, 1998.

BACKGROUND OF THE INVENTION

The invention relates to methods for implanting cells onto prosthetic materials, as well as methods for generating such implantable cells.

Despite prevention efforts, atherosclerotic disease remains a major cause of morbidity and mortality. Treatments for atherosclerotic disease range from medical management to interventional therapies, such as angioplasty, atherectomy, and bypass grafting. Bypass grafting with synthetic grafts has received much attention and has been used to treat many patients. Unfortunately, small caliber vascular grafts (i.e., grafts with inner diameters of less than 6 mm) generally have high failure rates, due largely to the thrombogenicity of the grafts. Thrombus deposits can form on the inner walls of the grafts, resulting in occlusions. In addition, intimal hyperplasia can occur, further contributing to the failure of small caliber grafts.

Several strategies for improving the success rates of these grafts have been developed. One such strategy is to increase the rate at which the graft becomes endothelialized, as endothelial cells have natural anti-thrombogenic properties that contribute to long-term graft patency. Moreover, it is believed that the presence of endothelial cells inhibits the development of neointimal hyperplasia at anastomotic regions. Endothelialization, which involves the migration of endothelial cells from adjacent tissue onto the luminal surface, can occur spontaneously when a graft is placed in a recipient. Unfortunately, endothelialization occurs to only a limited degree when prosthetic grafts are placed in human recipients, and the limited endothelialization that does occur takes place slowly.

To promote the rapid formation of an endothelial lining, endothelial cells can be seeded or sodded onto a graft before the graft is placed in the recipient. When the graft is placed in the recipient and exposed to physiologic blood flow, however, these cells are often washed away.

SUMMARY OF THE INVENTION

In general, the invention features a method for implanting cells onto a prosthesis; the method includes the steps of: (a) providing a prosthesis including a porous tube, where at least 25% of the pores on the inner surface of the tube have diameters of more than about 40 $\mu$m, at least 25% of the pores on the outer surface of the tube have diameters of less than about 30 $\mu$m, and the tube includes a substantially continuous layer of a biocompatible material; (b) contacting the prosthesis with a suspension of cells; and (c) providing a pressure differential between the inner surface and the outer surface, whereby the cells are retained in the pores of the inner surface. An example of a prosthesis that can be used is a vascular graft. The invention also features a sodded prosthesis formed by this method.

Preferably, at least 50% of the pores on the inner surface of the tube have diameters of more than about 40 $\mu$m, and at least 50% of the pores on the outer surface of the tube have diameters of less than about 30 $\mu$m. More preferably, at least 70%, or at least 90%, of the pores on the inner surface of the tube have diameters of more than about 40 $\mu$m, and at least 70%, or at least 90%, of the pores on the outer surface of the tube have diameters of less than about 30 $\mu$m.

In other preferred methods, at least 25% of the pores on the inner surface have diameters of more than about 50 $\mu$m, and more preferably have diameters of about 60 $\mu$m; in addition, at least 25% of the pores on the outer surface have diameters of less than about 20 $\mu$m, and more preferably have diameters of less than about 15 $\mu$m. More preferably, at least 50%, 70%, or 90% of the pores on the inner surface have diameters of more than about 50 $\mu$m, and more preferably have diameters of about 60 $\mu$m; in addition, at least 50%, 70%, or 90% of the pores on the outer surface have diameters of less than about 20 $\mu$m, and more preferably have diameters of less than about 15 $\mu$m.

Preferably, the pores on the inner surface and the pores on the outer surface are connected by gradually tapered openings.

In a related aspect, the invention features a method for implanting cells onto a prosthesis; the method includes the steps of: (a) providing a prosthesis including a porous tube, where the diameters of at least 25% of the pores on the inner surface of the tube are larger than the diameter of a human cell, such that human cells fit within the pores, the diameters of at least 25% of the pores on the outer surface of the tube are smaller than the diameter of a human cell, such that cells do not pass through the pores, and the tube includes a substantially continuous layer of a biocompatible material; (b) contacting the prosthesis with a suspension of cells; and (c) providing a pressure differential between the inner surface and the outer surface, whereby the cells are retained in the pores of the inner surface.

Preferably, the pores on the inner surface and the pores on the outer surface are connected by gradually tapered openings. In addition, the diameters of at least 50%, 70%, or 90% of the pores on the inner surface of the tube are preferably larger than the diameter of a human cell, and the diameters of at least 50%, 70%, or 90% of the pores on the outer surface of the tube are preferably smaller than the diameter of a human cell. The invention also features a sodded prosthesis formed by this method.

In another related aspect, the invention features a sodded vascular graft including a porous tube, where at least 25% of the pores on the inner surface of the tube have diameters of more than about 40 $\mu$m, at least 25% of the pores on the outer surface of the tube have diameters of less than about 30 $\mu$m, and the tube includes a substantially continuous layer of a biocompatible material; the graft has cells embedded in the pores of the inner surface. Preferably, the pores on the inner surface and the pores on the outer surface are connected by gradually tapered openings. In preferred grafts, at least 50%, 70%, or 90% of the pores on the inner surface of the tube have diameters of more than about 40 $\mu$m, and at least 50%, 70%, or 90% of the pores on the outer surface of the tube have diameters of less than about 30 $\mu$m.

In yet another related aspect, the invention features a sodded vascular graft including a porous tube, where the diameters of at least 25% of the pores on the inner surface of the tube are larger than the diameter of a human cell, the diameters of at least 25% of the pores on the outer surface of the tube are smaller than the diameter of a human cell, such that cells do not pass through the pores, and the tube includes a substantially continuous layer of a biocompatible material; the graft has cells embedded in the pores of the inner surface. Preferably, the pores on the inner surface and the pores on the outer surface are connected by gradually tapered openings. In preferred grafts, the diameters of at least 50%, 70%, or 90% of the pores on the inner surface of the tube are larger than the diameter of a human cell, and the diameters of at least 50%, 70%, or 90% of the pores on the outer surface of the tube are smaller than the diameter of a human cell.

In a final aspect, the invention features a method for obtaining an endothelial cell culture from a blood sample, the method involving: (a) obtaining a sample of mononuclear cells from a blood sample; and (b) culturing the sample of mononuclear cells, without further cell separation, on a cell adhesive polymer-coated solid support in the presence of endothelial growth factors.

In preferred embodiments, the blood sample is from a mammal (for example, a human) and the product of step (b) is an autologous endothelial cell sample; the blood sample is a peripheral blood sample; the mononuclear cells are obtained from the blood sample by centrifugation; the cell adhesive polymer is fibronectin; the solid support is a tissue culture plate; the endothelial growth factors include VEGF, bFGF, IGF, or any combination thereof; and the endothelial cell culture includes at least 90% endothelial cells or progenitors thereof.

As used herein, by "substantially continuous" is meant that a material, such as the material forming the walls of a prosthesis, consists essentially of a single layer having approximately constant, or gradually changing, physical characteristics.

By "gradually tapered" is meant that a dimension, such as pore size, changes in even, continuous gradations, rather than in discrete, sudden steps.

By "embedded" is meant that at least a portion of an object, such as a cell, infiltrates and is substantially enclosed by a surrounding structure or medium.

By "retained" is meant held in place. For a vascular graft, at least 20%, more preferably at least 50%, and most preferably at least 90%, of the cells remain in place in the graft under physiological blood flow conditions after a period of 14 days.

By an "endothelial cell culture" is meant a population of cells having at least 50%, preferably, at least 75%, more preferably, at least 80%, and, most preferably, at least 90% endothelial cells or progenitors thereof.

By a "blood sample" is meant any biological sample composed primarily of hematopoietic cells including, without limitation, a peripheral blood sample, bone marrow blood sample, or umbilical cord blood sample.

By a "sample of mononuclear cells" is meant a population of cells having at least 40%, preferably, at least 60%, more preferably, at least 75%, and, most preferably, at least 90% mononuclear cells.

By "cell separation" is meant any technique which physically subdivides a cell population including, without limitation, column chromatography, immunomagnetic separation, immunoprecipitation, and cell sorting techniques (for example, fluorescence-activated cell sorting).

By a "cell adhesive polymer" is meant any polymer which provides a substrate for endothelial cell attachment including, without limitation, fibronectin, vitronectin, laminin, keratin, gelatin, and collagen, with fibronectin being preferred.

By an "endothelial growth factor" is meant any protein which stimulates growth or differentiation of endothelial cells or their progenitors, including, without limitation, vascular endothelial cell growth factor (VEGF), basic fibroblast growth factor (bFGF), and insulin-like growth factor (IGF).

By a "solid support" is meant any solid surface which can support cell growth or differentiation including, without limitation, a tissue culture plate or well, bead, slide, column, bottle, or other vessel.

The cell implantation methods of the invention offer several advantages. For example, because the pores on the inner surfaces of the prostheses are relatively large, cells are retained on the inner surface, rather than being washed away by blood flow. The smaller pores on the outer surface of the prostheses prevent the cells from passing through the walls of the prosthesis. The smaller pores also help to maintain the structural integrity of the prosthesis and to reduce the propensity for bleeding that can occur, for example, in vascular grafts with uniformly large pores. These cell implantation methods therefore enhance cell retention without compromising the safety of the prostheses.

Furthermore, using the implantation methods of the invention, cells can be retained without the addition of adhesive substances such as the matrix proteins laminin and fibronectin, which are sometimes applied to the surface of prosthetic materials to enhance cell retention. As the presence of these proteins can lead to increased thrombogenicity, the ability to retain cells without them may increase the chances for a successful graft.

With respect to the methods for culturing endothelial cells to be implanted, the present invention again provides significant advantages. In particular, because the method described herein utilizes a standard blood sample as a source of endothelial cells, it avoids the need to obtain such cells by surgical removal of autologous veins or adipose tissue, thereby reducing patient trauma. Moreover, the present culture method provides a means for expanding an endothelial cell culture which does not require a physical cell separation step to remove unrelated, hematopoietic cells from the mononuclear blood fraction. The ability to dispense with this step makes the technique extremely rapid and quite cost-effective.

DETAILED DESCRIPTION

The invention features methods for implanting cells onto prosthetic materials, such as vascular grafts. In these methods, a prosthesis is combined with a suspension of cells, and a pressure differential is applied across the material to achieve implantation of the cells. The implanted cells are then able to withstand the shear forces that can disrupt layers of cells on the surfaces of prostheses exposed to blood flow.

Figure 1:
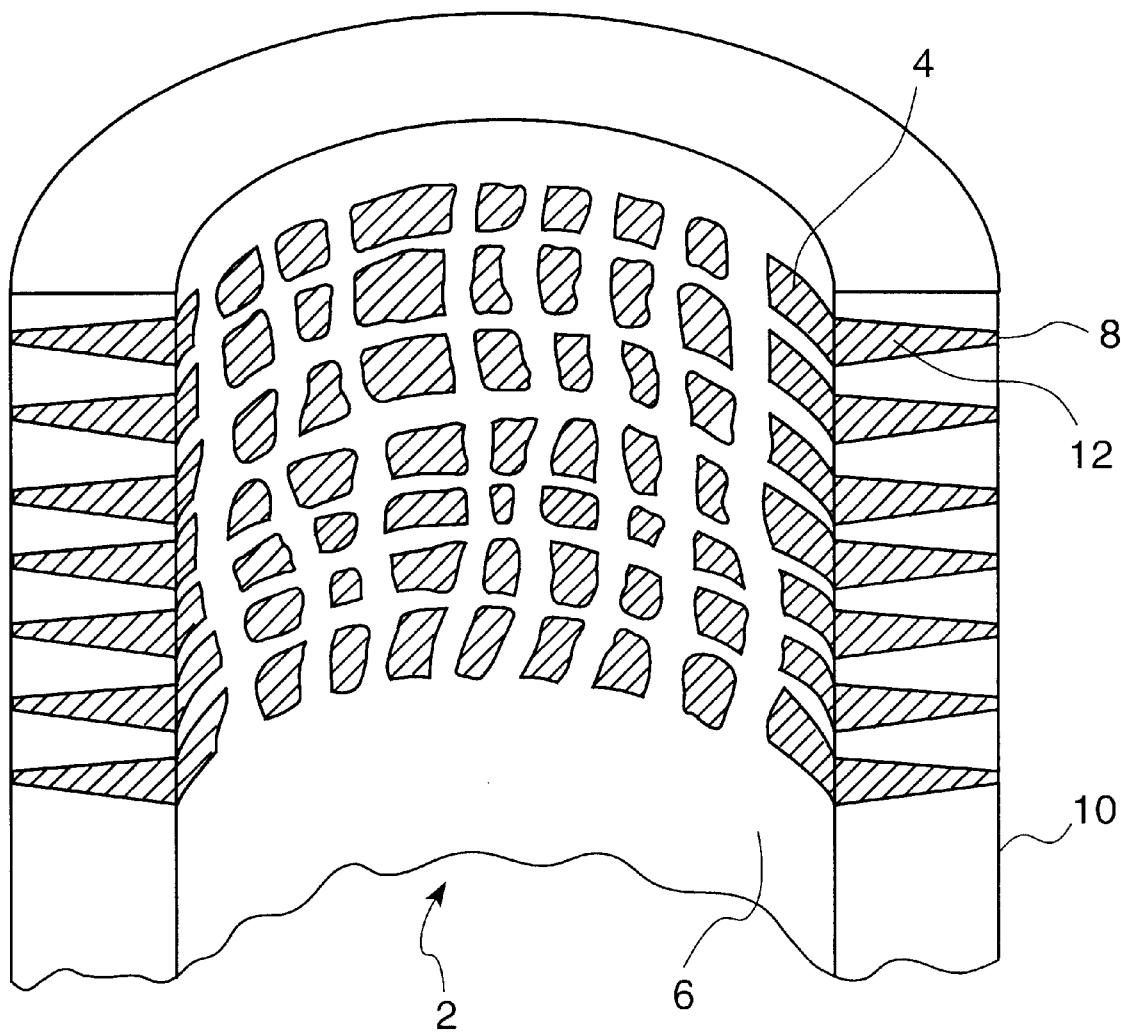
FIG. 1 is a cross-sectional view of an implantable tubular prosthesis.

One embodiment of the invention, a tubular prosthesis 2, is shown in FIG. 1. The cross sections of the pores in the figure appear to be rectangular or trapezoidal; the pores can also have a more rounded shape. As shown in FIG. 1, the pores 4 on the inner (i.e., luminal) surface 6 of the tube are larger than the pores 8 on the outer (i.e., abluminal) surface 10 of the tube. This structure allows cells to enter the interstitial space of the material to a limited depth, without allowing the cells to pass completely through the walls of the prosthesis.

The pores 4 on the inner surface 6 of the prosthesis 2 are preferably large enough to allow mammalian cells to enter;

i.e., the diameters of these pores are preferably larger than 40 µm. More preferably, they are larger than 50 µm, or 60 µm. The pores 8 on the outer surface 10 are preferably small enough to prevent cells from passing through these pores; i.e., the diameters of these pores are preferably smaller than 30 µm. More preferably, they are smaller than 20 µm, or 15 µm. The pore size changes gradually (rather than suddenly) upon moving from the inner surface of the tube to the outer surface, as shown in FIG. 1. The pores are connected by gradually tapered openings 12.

The prosthesis 2 can be made out of any biocompatible, porous material. Preferred materials include polytetrafluoroethylene (PTFE) and Dacron®. In one particular example, PTFE grafts with a 3 mm internal diameter are prepared using the techniques described in Martakos et al., U.S. Pat. No. 5,433,909. The grafts are prepared such that the pores on the inner surface are larger than the pores on the outer surface.

To obtain cells for sodding, any standard harvesting technique may be used. Examples of techniques for obtaining human cells are described in Jarrell et al., *J Vasc. Surg.* 13:733–734 (1991) and Jarrell et al., *Surgery* 100:392–399 (1986). The cells can be of any type suitable for transplantation purposes. For example, cells derived from autologous fat tissue, such as endothelial cells (primarily microvascular endothelial cells), fibroblasts, smooth muscle cells, and mesothelial cells, can be used. Cells obtained from other autologous tissue sources, such as blood vessels, skin, and omentum, can also be used. In addition, bone marrow cells, myoblasts, myocardial satellite cells, glial cells, pancreatic cells, blood cells, isolated progenitor or stem cells, or other endocrine cells derived from autologous, allogenic, or xenogenic sources, can be used in the methods of the invention.

If desired, the cells can be genetically engineered, prior to sodding, to enhance the functional characteristics of the prosthesis. Genetic modification may be achieved by using any recombinant viral vector or non-viral method of gene delivery. In one particular example, the cells can be transfected with a mammalian expression vector encoding the potent endothelial cell mitogen VEGF. Alternatively, standard homologous recombination and/or subsidiary techniques can be used with transient transfection in helper cell lines to generate recombinant, replication-deficient viral gene transfer vectors such as those for adenovirus, adeno-associated virus, retrovirus (e.g., VSVG-pseudotyped MMLV), herpesvirus, alphavirus, or lentivirus.

Other useful genes which may be expressed by implanted cells include, without limitation, genes for tissue plasminogen activator, hirudin, nitric oxide synthase, FGF, insulin, Factor VIII, and Factor IX. In general, the gene-modified endothelial cells on a graft may be used to deliver any therapeutic drug (for example, any angiogenic, anti-angiogenic, or anti-coagulant factor) to an individual. The genetic alteration does not significantly influence the successful retention of cells after surgical implantation of the prosthesis.

Figure 2:
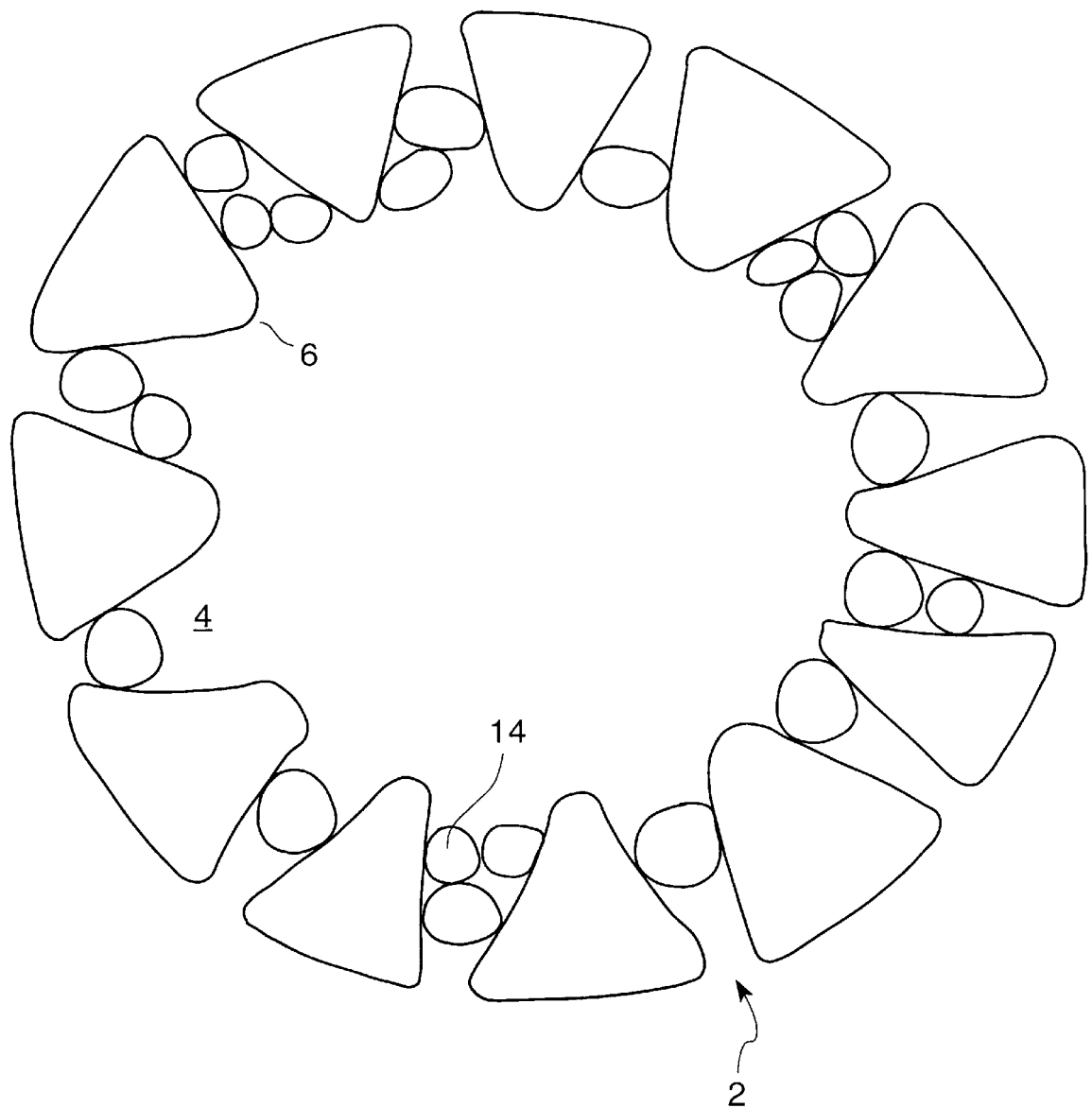
FIG. 2 is a cross sectional view of an implantable tubular prosthesis with cells embedded in the pores of the prosthesis.

To sod the cells onto the prosthesis 2 of FIG. 1, sodding medium containing the cells is injected into the lumen of the prosthesis. A pressure gradient is provided, in which the pressure on the interior of the prosthesis is higher than the pressure on the exterior, to filter the cell suspension through the prosthesis surface. The cells are thus embedded in the pores or the prosthesis. The sodding procedure can be repeated multiple times to further enhance the degree of cell implantation. As shown in FIG. 2, cells 14 become embedded in the relatively large pores 4 of the inner surface 6 of the prosthesis 2, and are thus retained within the prosthesis.

Using the methods of the invention, sodded prostheses can be cultured for short periods of time, for example, 8 to 12 hours, at 37° C. in a humidified, 5% $CO_2$ atmosphere, then placed into recipients. Alternatively, the prostheses can be placed into recipients immediately after the cells are sodded. In both instances, a large number of cells are retained in the large pores on the luminal surfaces of the prostheses. The methods of the invention allow for both improved retention of cells and efficient application of cells to the prosthesis, and may therefore reduce or eliminate the need for culturing periods.

It is desirable to minimize the culturing time required, as delays between seeding or sodding cells (particularly autologous cells) onto a prosthesis and implanting the prosthesis may decrease the benefits of implantation, prolong the therapeutic process, and/or increase the potential morbidity and cost of care. Previously known methods, for example, cell seeding methods, required longer periods of ex vivo culturing between cell seeding and implanting the prosthesis into the recipient.

There now follow particular examples of cell isolation, cell transfection, and cell sodding techniques. These examples are provided for the purpose of illustrating the invention, and should not be construed as limiting.

Cell Isolation, Culture, and Characterization

Rabbit adipose tissue derived cells (RATCs) were isolated from New Zealand White rabbit falciform ligament fat. 10–15 g subcutaneous fat was obtained from anesthetized rabbits. The fat was minced with scissors, incubated for 30 minutes at 37° C. with 8 mg/ml type 1 collagenase (Gibco BRL) and 8 mg/ml bovine serum albumin in Dulbecco's divalent cation free phosphate buffered saline. The mixture was centrifuged at 700 rpm for 5 minutes at 4° C. The pellet was re-suspended in PBS, centrifuged again, resuspended in M199 media with 20% fetal calf serum (FCS), and seeded onto 1% gelatin-coated plates. twenty minutes later, the cells were rinsed with PBS to remove red blood cells and unattached cells. The cells were cultured at 37° C. in a humidified, 5% $CO_2$ atmosphere. Cell yields were determined after trypsinization using a Coulter counter, and cell viability was determined with trypsin blue staining followed by examination on a hemocytometer. The culture medium was changed routinely, and the cells were passaged with 0.05% trypsin-EDTA (Gibco-BRL) and replated on uncoated plastic dishes at a split ratio of 1:3. Cells from passages 2 to 9 were used.

Gene Transfer Vectors

A mammalian expression vector encoding human $VEGF_{165}$ (pcDNAhVEGF) was prepared from pLen-165 as described in Tischer et al., *J. Biol. Chem.* 266(18): 11947–11954 (1991) and Tischer et al., *Biochem. Biophys. Res. Commun.* 165(3): 1198–1206 (1989). A Bam HI fragment, containing the sequences for human $VEGF_{165}$, was ligated to the BamHI site of the expression vector pcDNA3 (Invitrogen). The orientation was confirmed by digestion of the resultant plasmid with AflIII.

RATC Transfection

Cells were plated at $3-4 \times 10^5$ cells/cm² in 6 well plates or 2 well chamber slides. One day later, the media was removed, and the cells were rinsed and incubated with a DNA-liposome complex (1 µg DNA:12 µl lipofectamine, Gibco-Brl) in 1 ml Opti-MEM.

Cell Sodding into Vascular Prosthesis

A 5-cm segment of a PTFE graft was clamped at one end with hemostatic forceps, connected at the other end to a T connector, and placed in a container, which collects the flow-through. The graft was pressurized using a 10-ml syringe filled with sodding medium. Thirty to 60 minutes prior to cell sodding, sodding media (serum-free medium 199) was injected into the lumen through the interstices of the graft using a 10-ml syringe. The sodding media was then removed and replaced with 3 ml media containing 200 μg heparin plus rabbit adipose tissue cells (4–6×10$^5$ cells/cm$^2$) harvested 1 day after transfection with the pcDNAh-VEGF$_{165}$ vector. Five ml of media was pushed through the graft to filter the cell suspension through the graft surface. The fluid which passed through the graft was examined and found to be devoid of cells.

Blood-Derived Endothelial Cell Culture

In an alternative approach, endothelial cells for implantation may be obtained from a blood sample (for example, from a human patient) and cultured in the presence of endothelial growth factors. In animal model experiments, this approach was carried out as follows.

Heparinized whole blood samples were obtained from anesthetized animals via cannulation of the right femoral artery or vein. Mononucleated cells were separated by density gradient centrifugation using 1.077 g/mL Ficoll solution (Amersham Pharmacia). Cells were plated on fibronectin-coated plastic (Panvera, Calif.) in Endothelial Growth Media (EGM, Clonetics, San Diego, Calif.) supplemented with saturating concentrations of endothelial cell growth factors (vascular endothelial cell growth factor, basic fibroblast growth factor, and insulin like growth factor; EGM 2-MV singlequots, Clonetics). These culture conditions resulted in selective attachment and differentiation of early endothelial progenitor cells. Cultures were expanded in vitro for a period of 10–14 days. Autologous endothelial cells prepared in this manner may be used, with or without prior genetic modification (as described above), for seeding or sodding onto prosthetic vascular grafts (also as described above).

This approach of endothelial cell culture may also be used for the propagation of autologous human endothelial cells, using a blood sample isolated from a patient by any standard technique. Mononucleated cells may be harvested by any method which results in isolation of the "buffy coat" fraction, including, without limitation, standard density gradient centrifugation. In addition, the endothelial cell culture medium described above may be replaced by the medium described in Shi et al. (Blood 15;92: 362–7, 1998).

The endothelial cell culture technique described herein may be combined with any method of cell seeding or sodding, for example, those methods described herein, to provide vascular bioprostheses.

The ability to readily produce autologous endothelial cells from patient blood samples augments the implantation technique described above. In particular, the presence of an endothelial cell monolayer on the luminal side of a graft prior to implantation is associated with improved performance of the graft itself. The reduced thrombogenicity of the prosthetic surface due to the impregnation with autologous endothelial cells results in better function outcome. Small caliber prosthetic vascular grafts (i.e., those having internal diameters less than or equal to 4 mm) are known to have very high failure rates in humans (i.e., due to early thrombotic occlusion) and are therefore greatly benefitted by the presence of an intact endothelial cell monolayer.

Use

The methods of the invention can be used to prepare prostheses, especially vascular grafts, for implantation into recipients. The methods can be used to prepare small caliber vascular grafts and to prepare vascular grafts that can be placed in the heart, where currently available artificial grafts cannot be used. The methods can also be used to sod genetically altered cells onto prostheses to allow delivery of recombinant or molecular therapies, or to enhance tissue compatibility.

These techniques may be used in humans or any other mammal.

Other Embodiments

From the foregoing description, it will be apparent that variations and modifications may be made to the invention described herein to adopt it to various usages and conditions. Such embodiments are also within the scope of the following claims.

All publications and patents mentioned in this specification are herein incorporated by reference to the same extent as if each individual publication or patent was specifically and individually indicated to be incorporated by reference.

What is claimed is:

1. A method for implanting cells onto a prosthesis comprising the steps of:
   (a) providing a prosthesis comprising a porous tube, wherein at least 25% of the pores on the inner surface of said tube have diameters of more than about 40 μm and at least 25% of the pores on the outer surface of said tube have diameters of less than about 30 μm, wherein said tube comprises a substantially continuous layer of a biocompatible material, and wherein said pores on said inner surface and said pores on said outer surface are connected by gradually tapered openings;
   (b) contacting said prosthesis with a suspension of cells; and
   (c) providing a pressure differential between said inner surface and said outer surface, whereby said cells are retained in said pores of said inner surface.

2. The method of claim 1, wherein at least 50% of said pores on said inner surface have diameters of more than about 40 μm, and at least 50% of said pores on said outer surface have diameters of less than about 30 μm.

3. The method of claim 1, wherein at least 70% of said pores on said inner surface have diameters of more than about 40 μm, and at least 70% of said pores on said outer surface have diameters of less than about 30 μm.

4. The method of claim 1, wherein at least 90% of said pores on said inner surface have diameters of more than about 40 μm, and at least 90% of said pores on said outer surface have diameters of less than about 30 μm.

5. The method of claim 1, wherein at least 25% of said pores on said inner surface have diameters of more than about 50 μm, and at least 25% of said pores on said outer surface have diameters of less than about 20 μm.

6. The method of claim 1, wherein at least 50% of said pores on said inner surface have diameters of more than about 50 μm, and at least 50% of said pores on said outer surface have diameters of less than about 20 μm.

7. The method of claim 1, wherein at least 25% of said pores on said inner surface have diameters of more than about 60 μm, and at least 25% of said pores on said outer surface have diameters of less than about 15 μm.

8. The method of claim 1, wherein at least 50% of said pores on said inner surface have diameters of more than about 60 μm, and at least 50% of said pores on said outer surface have diameters of less than about 15 μm.

9. The method of claim 1, wherein said prosthesis is a vascular graft.

10. A sodded prosthesis formed by the method of claim 1.

11. A method for implanting cells onto a prosthesis comprising the steps of:

(a) providing a prosthesis comprising a porous tube, wherein
  (i) the diameters of at least 25% of the pores on the inner surface of said tube are larger than the diameter of a human cell, such that human cells fit within said pores,
  (ii) the diameters of at least 25% of the pores on the outer surface of said tube are smaller than the diameter of a human cell, such that cells do not pass through said pores,
  (iii) said tube comprises a substantially continuous layer of a biocompatible material, and
  (iv) said pores on said inner surface and said pores on said outer surface are connected by gradually tapered openings;
(b) contacting said prosthesis with a suspension of cells; and
(c) providing a pressure differential between said inner surface and said outer surface, whereby said cells are retained in said pores of said inner surface.

12. A sodded prosthesis formed by the method of claim 11.

* * * * *